United States Patent [19]

Kobayashi et al.

[11] 4,396,785
[45] Aug. 2, 1983

[54] 3,3,3-TRIFLUOROPROPYL DERIVATIVES OF NAPHTHALENE OR METHYLNAPHTHALENE AND PROCESS FOR PREPARING THE SAME

[75] Inventors: Yoshiro Kobayashi, Tokyo; Itsumaro Kumadaki, Hachiohji; Masaaki Takahashi, Tokyo; Takashi Yamauchi, Iwaki, all of Japan

[73] Assignee: Kureha Kagaku Kogyo Kabushiki Kaisha, Tokyo, Japan

[21] Appl. No.: 290,931

[22] Filed: Aug. 7, 1981

[30] Foreign Application Priority Data

Sep. 1, 1980 [JP] Japan .............................. 55-120927
Dec. 29, 1980 [JP] Japan .............................. 55-186565
Jan. 27, 1981 [JP] Japan .............................. 56-10642

[51] Int. Cl.$^3$ .......................................... C07C 17/32
[52] U.S. Cl. ................................. 570/129; 570/144; 252/581
[58] Field of Search ................ 570/129, 144; 252/581

[56] References Cited
U.S. PATENT DOCUMENTS
2,561,738  7/1951  Hill ...................................... 252/581

Primary Examiner—Charles F. Warren
Assistant Examiner—Joseph A. Boska
Attorney, Agent, or Firm—Wegner & Bretschneider

[57] ABSTRACT

Novel 3,3,3-trifluoropropyl derivatives of naphthalene or methylnaphthalene of the general formula

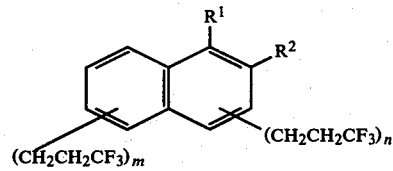

wherein $R^1$ and $R^2$ respectively represent hydrogen atom or methyl group, with the proviso that $R^1$ and $R^2$ do not simultaneously represent methyl group; m and n respectively represent zero or 1, with the proviso that the sum of m and n is 1, and a process for preparing the derivatives are disclosed. The derivatives are suitable as a dielectric material.

11 Claims, 6 Drawing Figures

3,3,3-TRIFLUOROPROPYL DERIVATIVES OF NAPHTHALENE OR METHYLNAPHTHALENE AND PROCESS FOR PREPARING THE SAME

BACKGROUND AND DETAILED DESCRIPTION OF THE INVENTION

The present invention relates to certain novel 3,3,3-trifluoropropyl derivatives of naphthalene, 1-methylnaphthalene or 2-methylnaphthalene, and to a novel process for preparing the derivatives.

As a means for synthesizing an aromatic compounds having benzene ring substituted by 3,3,3-trifluoropropyl group, only one process has been proposed (U.S. Pat. No. 3,080,428), in which 3,3,3-trifluoropropyl ether, $(CF_3CH_2CH_2)_2O$, is brought into reaction with benzene in the presence of hydrogen fluoride to obtain (3,3,3-trifluoropropyl)benzene. However, since in the above-mentioned process, water is formed by the reaction, the activity of the catalyst is reduced during the reaction, and the recovery of once-used catalyst is difficult. Moreover, 3,3,3-trifluoropropyl ether as the starting material is synthesized by the reaction of hydrogen fluoride, formaldehyde (or its polymer) and vinylidene fluoride. Accordingly, 3,3,3-trifluoropropyl ether is expensive because of the high price of vinylidene fluoride and of the yield of synthesizing the ether as low as 50 to 60%.

It is an object of the present invention to provide a novel 3,3,3-trifluoropropyl derivative of naphthalene, 1-methylnaphthalene or 2-methylnaphthalene of the general formula

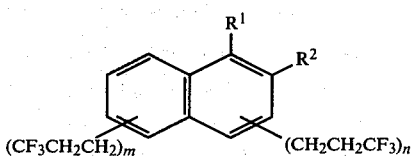

wherein $R^1$ and $R^2$ respectively represent hydrogen atom or methyl group, with the proviso that $R^1$ and $R^2$ does not simultaneously represent methyl group; m and n respectively represent zero or 1, with the proviso that the sum of m and n is 1.

Another object is to provide a novel process for preparing the 3,3,3-trifluoropropyl derivative of naphthalene, 1-methylnaphthalene or 2-methylnaphthalene, which comprises bringing 3,3,3-trifluoropropene into reaction with naphthalene, 1-methylnaphthalene or 2-methylnaphthalene in the presence of an acid catalyst selected from the group consisting of hydrogen fluoride and boron trifluoride. A still further object is to provide a dielectric material comprising at least one of the 3,3,3-trifluoropropyl derivatives of naphthalene, 1-methylnaphthalene or 2-methylnaphthalene. A particular object is to provide 3,3,3-trifluoropropyl derivatives of naphthalene, 1-methylnaphthalene or 2-methylnaphthalene obtained by bringing 3,3,3-trifluoropropene into reaction with naphthalene, 1-methylnaphthalene or 2-methylnaphthalene in the presence of an acid catalyst, and separating the thus formed 3,3,3-trifluoropropyl derivative from the reaction mixture. Other objects will appear hereinafter in the description.

BRIEF DESCRIPTION OF DRAWING

In Drawing

Figure 1:
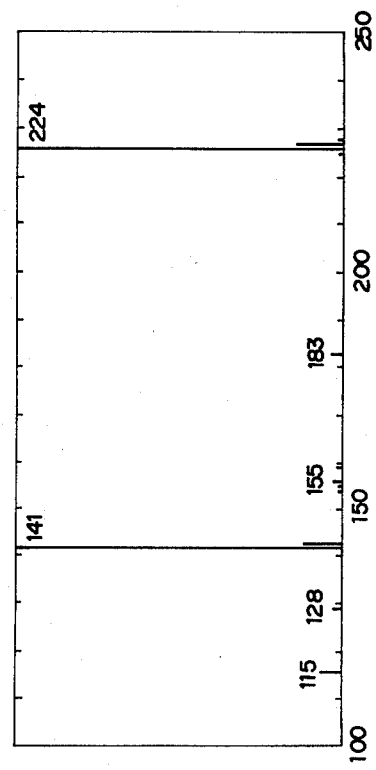
FIGS. 1 and 2 respectively show the infrared absorption spectrum and the mass spectrum of naphthalene singly substituted by 3,3,3-trifluoropropyl group.

The compound of the present invention is obtainable by using naphthalene, 1-methylnaphthalene or 2-methylnaphthalene and 3,3,3-trifluoropropene as the starting material in the presence of an acid catalyst such as hydrogen fluoride and boron trifluoride under normal pressure or pressure conditions either continuously or in batch wise.

The reaction formula is set forth below.

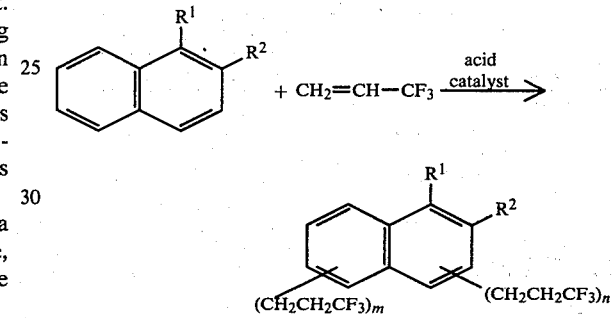

wherein $R^1$, $R^2$, m and n are as defined above.

For instance, in a case of batch system, an acid catalyst, 3,3,3-trifluoropropene and an aromatic compound of naphthalene, 1-methylnaphthalene or 2-methylnaphthalene are charged into a stainless-steel autoclave, and the content is brought into reaction for 0.5 to 30 hours at a temperature of −20° to 100° C. in the case of using boron trifluoride as the catalyst, or 0° to 120° C. in the case of using hydrogen fluoride. Preferable reaction temperature in the aromatic compounds are respectively shown in the following table 1.

TABLE 1

| Aromatic compound as the starting material | Reaction temperature (°C.) HF | BF$_3$ |
| --- | --- | --- |
| Naphthalene | 80 ~ 120 | 0 ~ 100 |
| 1-Methylnaphthalane | 0 ~ 80 | −20 ~ 50 |
| 2-Methylnaphthalene | 0 ~ 80 | −20 ~ 50 |

After the reaction is over, residual gas is removed from the reaction system and after removing the catalyst from the reaction mixture, it is subjected to distillation under a reduced pressure to recover the object product, naphthalene, 1-methylnaphthalane or 2-methylnaphthalene substituted by 3,3,3-trifluoropropyl group, as a colourless and transparent liquid.

The compound of the present invention is excellent in electrical properties and is utilizable as an insulating material, particularly as an insulating oil.

Since the dielectric constant of the compound of the present invention is excellent presumably owing to its 3,3,3-trifluoropropyl group, the compound of the present invention may be applied as an insulating oil for a capacitor or a condenser, and it can be expected that the compound of the present invention will contribute to the improvement of performances and miniaturization of the capacitor and the apparatus using the capacitor(s).

The present invention will be explained more in detail while referring to the non-limiting examples as follows:

EXAMPLE 1

In a 1-liter stainless-steel autoclave, 320 g of naphthalene and 264 g of 3,3,3-trifluoropropene were introduced, and then boron trifluoride was charged thereinto until the internal pressure of the autoclave became 60 kg/cm$^2$.gauge. The reaction was carried out at 60° C. for 20 hours. After the reaction was over, the content of the autoclave was extracted with toluene, and the extract was washed with water and dried following conventional procedures. According to the results of analysis by gas chromatography and mass spectra, the reaction product showed the following data as in Table 2:

TABLE 2

| Compound | Percentage of the area of the specific peak to the total area of the peaks |
| --- | --- |
| Naphthalene | 7.6 |
| Mono-(3,3,3-trifluoropropyl)-naphthalene | 51.7 |
| Bis-(3,3,3-trifluoropropyl)-naphthalene | 35.7 |
| Tris-(3,3,3-trifluoropropyl)-naphthalene | 4.7 |
| Other | 0.3 |

In the next step, the reaction product was subjected to fractional distillation under 2 mmHg to obtain a fraction distilling at 94° to 95° C. This fraction was confirmed to be (3,3,3-trifluoropropyl)naphthalene of a purity of not lower than 99% by gas chromatography and the following analytical data:

(a) Mass spectroscopical data: m/e: 224 (20 eV)

FIG. 1 shows the mass spectrum near the parent peak.

(b) Nuclear magnetic resonance spectrum

No signal of methyl group was observed in $^1$H-NMR, and a triplet of trifluoromethyl group was observed near +2.7 ppm from benzotrifluoride as the external standard in $^{19}$F-NMR.

(c) Infrared absorption spectroscopical data

Figure 2:
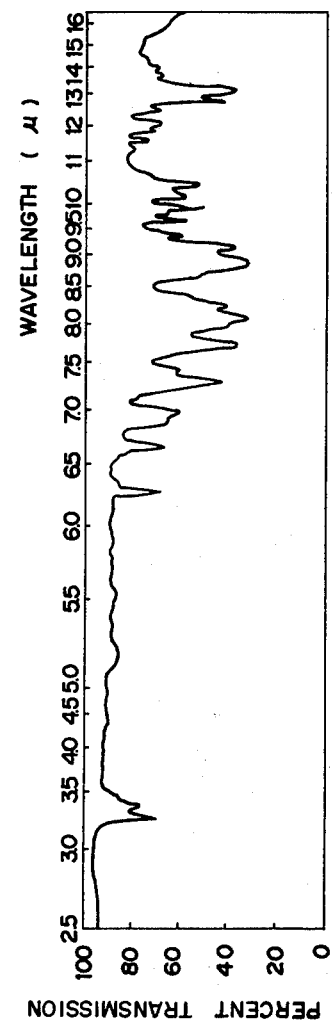

FIG. 2 shows the infrared absorption spectrum.

(d) Elementary analytical data

| | found (%) | calcd. for C$_{13}$H$_{11}$F$_3$ (%) |
| --- | --- | --- |
| C | 69.4 | 69.6 |
| H | 5.0 | 4.9 |
| F | 25.6 | 25.5 |

(e) Boiling point: 94–95/2 mmHg

Specific gravity: 1.195 at 27° C.
Refractive index: 1.525 at 25° C.

The electrical properties of the fraction at 25° C. are shown below in Table 3.

TABLE 3

| | |
| --- | --- |
| Dielectric constant: | 5.25 |
| Dielectric loss (tan δ) (%): | 0.24 |
| Volume resistivity (Ω · cm): | 3.37 × 10$^{14}$ |

EXAMPLE 2

Into a 1-liter stainless-steel autoclave, 355 g of 1-methylnaphthalene, 250 g of 3,3,3-trifluoropropene was introduced, and boron trifluoride was charged thereinto until the inner pressure of the autoclave became 62 kg/cm$^2$.gauge. The reaction was carried out at room temperature for 20 hours. After the reaction was over, the gas in the autoclave was purged and the content of the autoclave was washed out with dichloromethane. The washed-out material was washed with water and dried after conventional procedures and then dichloromethane was distilled out by using a rotary evaporator from the dried material to obtain 535 g of reaction mixture. By fractionally distilling the reaction mixture under 2.8 mmHg, a fraction distilling at 108° to 114° C. was obtained. It was confirmed that the present fraction was 1-methyl-3,3,3-trifluoropropylnaphthalene of a purity of not less than 99% from the gas chromatographical data and the following analytical data:

(a) Mass spectroscopical data: m/e=238 (20 eV)

Figure 3:
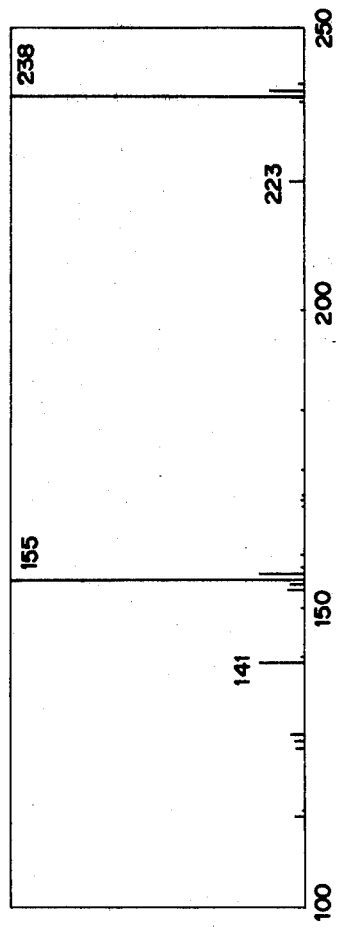
FIGS. 3 and 4 show respectively those of 1-methylnaphthalene mono-substituted by 3,3,3-trifluoropropyl group and FIGS. 5 and 6 respectively show those of 2-methylnaphthalene mono-substituted by 3,3,3-trifluoropropyl group.

FIG. 3 shows the mass spectrum of the fraction near the parent peak.

(b) Nuclear magnetic resonance spectrum: in carbon tetrachloride $^1$H-NMR δ 2.0~3.6 ppm (m, 7H: —CH$_2$— and —CH$_3$)

δ 7.0~8.1 ppm (m, 6H: Aromatic H)

(c) Infrared absorption spectroscopical data

Figure 4:
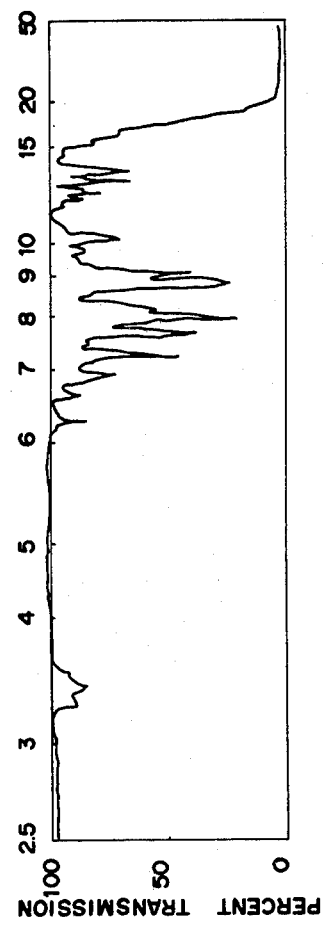

FIG. 4 shows the infrared absorption spectrum of the fraction.

(d) Elementary analytical data

| | found (%) | calcd. as C$_{14}$H$_{13}$F$_3$ |
| --- | --- | --- |
| C | 70.3 | 70.59 |
| H | 5.5 | 5.46 |
| F | 24.2 | 23.95 |

(e) Boiling point: 108°–114° C./2.8 mmHg

Specific gravity: 1.186 at 20° C.
Refractive index: 1.5324 at 20° C.

The electrical properties of the fraction at 20° C. are shown below in Table 4.

TABLE 4

| | |
| --- | --- |
| Dielectric constant: | 5.1 |
| Dielectric loss (tan δ) (%): | 0.20 |
| Volume resistivity (Ω · cm): | 3.1 × 10$^{14}$ |

EXAMPLE 3

Into a 1-liter stainless-steel autoclave, 356 g of 2-methylnaphthalene and 250 g of 3,3,3-trifluoropropene were introduced, and boron trifluoride was then charged thereinto until the inner pressure of the autoclave became 68 kg/cm$^2$.gauge. The reaction was carried out for 17 hours at 10° C. After the reaction was over, the gas in the autoclave was purged and the content of the autoclave was washed out with dichloromethane. After the washed-out material was washed with water and dried following conventional procedures, dichloromethane was distilled out from the washed-out material by using a rotary evaporator to obtain the reaction product.

On subjecting the reaction product to fractional distillation under a reduced pressure of 2 mmHg, 63.2 g of a fraction distilling at 100°–104° C./2 mmHg was obtained. According to the gas chromatographical data and the following analytical data, the fraction was confirmed to be 2-methyl-(3,3,3-trifluoropropyl)naphthalene of a purity not less than 99%:

(a) Mass spectroscopical data: m/e=238 (20 eV)

Figure 5:
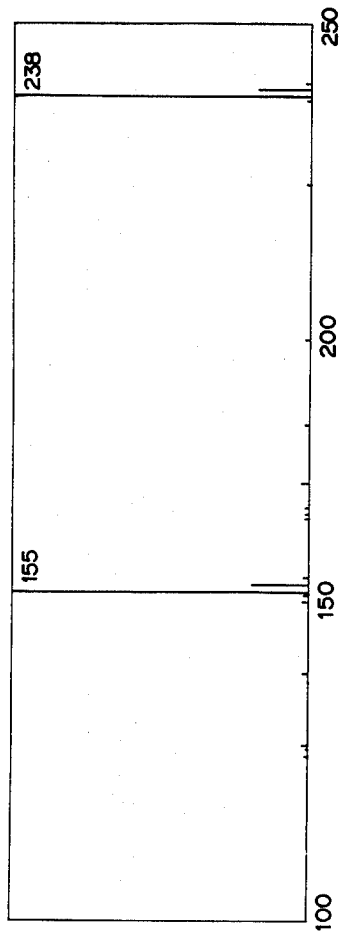

FIG. 5 shows the mass spectrum of the fraction near the parent peak.

(b) Nuclear magnetic resonance spectrum in carbon tetrachloride $^1$H-NMR $\delta$ 1.8~3.5 ppm (m, 7H: —CH$_2$— and —CH$_3$)

$\delta$ 6.8~8.1 ppm (m, 6H: aromatic H)

(c) Infrared absorption spectrum

Figure 6:
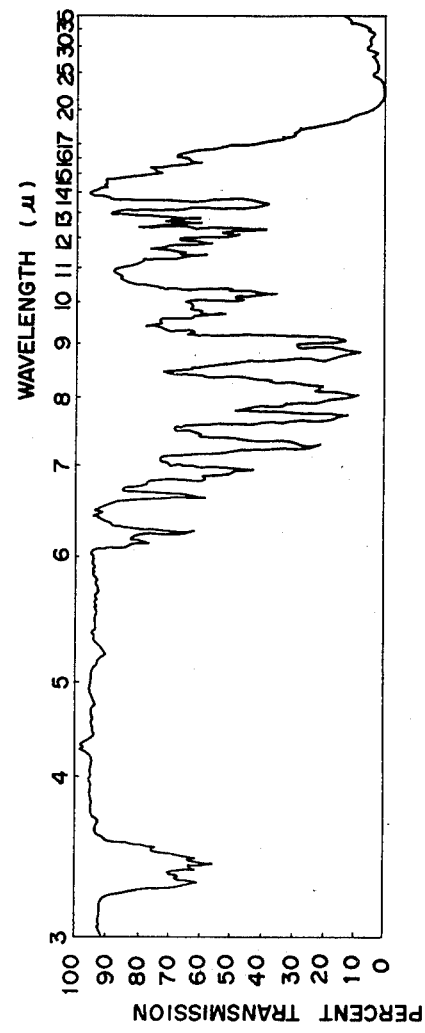

FIG. 6 shows the infrared absorption spectrum of the fraction.

(d) Elementary analytical data

|   | found (%) | calcd. as C$_{14}$H$_{13}$F$_3$ |
|---|---|---|
| C | 70.1 | 70.59 |
| H | 5.5 | 5.46 |
| F | 24.4 | 23.95 |

(e) Boiling point: 100°–104° C./2 mmHg

Specific gravity: 1.166 at 20° C.
Refractive index: 1.5306 at 20° C.

The electrical properties of the fraction at 20° C. are shown below in Table 5.

TABLE 5

| Dielectric constant: | 5.08 |
| Dielectric loss (tan $\delta$) (%): | 0.24 |
| Volume resistivity ($\Omega \cdot$ cm): | 2.50 × 10$^{14}$ |

What is claimed is:

1. A naphthalene derivative of the formula:

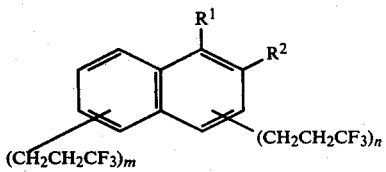

wherein R$^1$ and R$^2$ respectively represent hydrogen atom or methyl group, with the proviso that R$^1$ and R$^2$ do not simultaneously represent methyl group; m and n respectively represent zero or 1, with the proviso that the sum of m and n is 1.

2. (3,3,3-Trifluoropropyl)naphthalene.
3. 1-Methyl-(3,3,3-trifluoropropyl)naphthalene.
4. 2-Methyl-(3,3,3-trifluoropropyl)naphthalene.
5. A process for preparing 3,3,3-trifluoropropyl derivative of an aromatic compound selected from the group consisting of naphthalene, 1-methylnaphthalene and 2-methylnaphthalene, said process comprising bringing said aromatic compound into reaction with 3,3,3-trifluoropropene in the presence of an acid catalyst selected from the group consisting of hydrogen fluoride and boron trifluoride.
6. The process according to claim 5, wherein the aromatic compound is brought into reaction with 3,3,3-trifluoropropene in the presence of boron trifluoride at a temperature of −20° to 100° C. for 0.5 to 30 hours.
7. The process according to claim 5, wherein the aromatic compound is brought into reaction with 3,3,3-trifluoropropene in the presence of hydrogen fluoride at a temperature of 0° to 120° C. for 0.5 to 30 hours.
8. A dielectric material comprising at least one of 3,3,3-trifluoropropyl aromatic compound of the formula

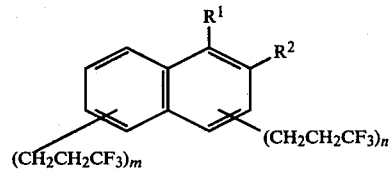

wherein R$^1$ and R$^2$ respectively represent hydrogen atom or methyl group, with the proviso that R$^1$ and R$^2$ do not simultaneously represent methyl group; m and n respectively represent zero or 1, with the proviso that the sum of m and n is 1.

9. A mono-substituted naphthalene by 3,3,3-trifluoropropyl group obtained by bringing naphthalene into reaction with 3,3,3-trifluoropropene in the presence of an acid catalyst selected from the group consisting of hydrogen fluoride and boron trifluoride, and separating said mono-substituted naphthalene from the resultant reaction mixture.

10. A mono-substituted 1-methylnaphthalene by 3,3,3-trifluoropropyl group obtained by bringing 1-methylnaphthalene into reaction with 3,3,3-trifluoropropene in the presence of an acid catalyst selected from the group consisting of hydrogen fluoride and boron trifluoride, and separating said mono-substituted 1-methylnaphthalene from the resultant reaction mixture.

11. A mono-substituted 2-methylnaphthalene by 3,3,3-trifluoropropyl group obtained by bringing 2-methylnaphthalene into reaction with 3,3,3-trifluoropropene in the presence of an acid catalyst selected from the group consisting of hydrogen fluoride and boron trifluoride, and separating said mono-substituted 2-methylnaphthalene from the resultant reaction mixture.

* * * * *